United States Patent [19]

Chaloner-Gill

[11] Patent Number: 5,393,621
[45] Date of Patent: Feb. 28, 1995

[54] FIRE-RESISTANT SOLID POLYMER ELECTROLYTES

[75] Inventor: Benjamin Chaloner-Gill, Santa Clara, Calif.

[73] Assignee: Valence Technology, Inc., San Jose, Calif.

[21] Appl. No.: 139,229

[22] Filed: Oct. 20, 1993

[51] Int. Cl.⁶ .............................................. H01M 6/18
[52] U.S. Cl. ..................................... 429/192; 252/62.2
[58] Field of Search ................... 429/192; 252/62.2; H01M 6/18

[56] References Cited

U.S. PATENT DOCUMENTS

| | | |
|---|---|---|
| 2,616,873 | 11/1952 | Cass . |
| 4,731,705 | 3/1988 | Velasco et al. ................ 252/62.2 X |
| 4,737,422 | 4/1988 | Knight et al. . |
| 5,114,809 | 5/1992 | Nakacho et al. .................... 429/192 |

OTHER PUBLICATIONS

Abraham et al., J. Electrochemical Soc., 138 (Apr./1991) p. 921.

Primary Examiner—John S. Maples
Attorney, Agent, or Firm—Russell La Paglia

[57] ABSTRACT

Solid polymeric electrolytes are composed of a solid polymeric matrix formed by polymerization of organophosphorus compounds.

18 Claims, No Drawings

FIRE-RESISTANT SOLID POLYMER ELECTROLYTES

FIELD OF THE INVENTION

The invention relates to polymers for solid polymeric electrolytes and their use in solid electrochemical cells. The invention particularly relates to novel phosphorous-containing, single-phase, solid polymeric electrolytes.

BACKGROUND OF THE INVENTION

Electrochemical cells containing an anode, a cathode and a solid, solvent-containing electrolyte incorporating a salt are known in the art and are usually referred to as "solid batteries". These cells offer a number of advantages over electrochemical cells containing a liquid electrolyte (i.e., "liquid batteries").

Typically, solid batteries employ a solid electrolyte interposed between a cathode and an anode. The solid electrolyte contains either an inorganic or an organic matrix and a suitable salt, such as an inorganic ion salt, and preferably an electrolyte solvent as separate components. The inorganic matrix may be non-polymeric, e.g., $\beta$-alumina, silver oxide, lithium iodide, and the like, or polymeric, e.g., inorganic (polyphosphazene) polymers, whereas the organic matrix is typically polymeric. Organic polymeric matrices for use as solid electrolytes are well known in the art and are typically organic polymers obtained by polymerization of a suitable organic monomer as described, for example, in U.S. Pat. No. 4,908,283. Suitable organic monomers include, by way of example, ethylene oxide, propylene oxide, ethyleneimine, epichlorohydrin, ethylene succinate, and an acryloyl-derivatized alkylene oxide containing at least one acryloyl group of the formula $CH_2=CR'C(O)O-$ where R' is hydrogen or a lower alkyl of from 1–6 carbon atoms.

The preferred solid polymeric electrolyte is typically composed of an inorganic ion salt, a low molecular weight compatible solvent and a solid polymeric matrix which is formed by polymerization of an organic monomer or prepolymer. A distinction is made in the art between those solid electrolytes which contain a low molecular weight solvent (i.e., a solvent electrolyte or plasticizer) and those solid electrolytes which do not contain such solvents, Fiona M. Gray, "Solid Polymer Electrolytes", ibid., pages 1–2 and pages 108–109.

Solid polymeric electrolytes have many advantageous properties for the fabrication of electrochemical cells and batteries such as: ionic conductivity, thermal stability, reduced corrosion of the electrodes, cyclability, mechanical flexibility, compactness and low self-discharge rates. Solid polymeric electrolytes permit us to create electrochemical sources of high energy per unit weight. Solid electrolytes and particularly polymeric electrolytes have a principal advantage in being prepared in thin layers which reduces cell resistance and allows large drains at low current densities. The subject has been treated in several recent publications, i.e. Fiona M. Gray, "Solid Polymer Electrolytes", VCH Publishers, Inc., New York, 1991; and M. Gauthier, et al., "Solid Polymer Electrolyte Lithium Batteries", Chapter 9, in "Polymer Electrolyte Reviews", eds. J. R. MacCallum and C. A. Vincent, Elsevier, New York, 1989, which are incorporated herein by reference in their entirety.

Thus, it is stated in the art that the polymeric electrolyte plays several roles in the solid polymer battery. First, it is an ionic conductor that can be made very thin to improve the energy density of the battery. It is also a flexible mechanical interelectrode separator which eliminates the need for an inert porous separator. Finally, it is a binder and an adhesive which ensures good mechanical and electrical contact between the electrodes. The present invention adds several additional benefits to the art of solid polymeric electrolytes.

The solid polymeric matrix of which the solid polymeric electrolyte is composed is preferably an organic polymer. The prior art favors poly(ethylene oxide) of molecular weight from 1,000 to over 100,000, substituted with crosslinkable groups such as acrylates and vinyls. Cross-linking is achieved by thermal or radiation treatments of the polymer, U.S. Pat. Nos. 4,908,283, 4,830,939 and 5,037,712. Chemical cross-linking has also been suggested, U.S. Pat. No. 3,734,876.

Besides poly(oxyethylene) homopolymers, i.e. poly(ethylene oxide), it has been found that copolymers containing poly(oxyethylene) groups can be used as in solid polymer electrolytes when copolymerized with siloxanes, K. Nagaoka, et at., J.Polym. Sci. Polym. Lett. Ed.22, 659 (1984); Phosphazene, P. M. Blonsky, et at., J. Am. Chem. Soc., 106, 6854 (1984); Urethanes, A. Bouridah et at., Solid State Ionics, 15,233 (1985); or Cross-linked with Phosphorous Oxychloride, J. R. M. Giles, et at., Solid State Ionics, 24, 155 (1987), Polym. Commun. 27, 360 (1987). Phosphazene monomers and the, resulting polyphosphazene solid matrix are disclosed by Abraham et al., Proc. Int. Power Sources Syrup., 34th, pp. 81–83 (1990) and by Abraham et al., J. Electrochemical Society, Vol. 138, No. 4, pp. 921–927 (1991). Phosphonitrilic polymers, or phosphazene polymers, as they are also called, are inorganic-type polymers of recent discovery. The repeating backbone unit of the polyphosphazines, (N=P), displays their inorganic character, M. P. Stevens, "Polymer Chemistry, "2nd Edition, Oxford Press, New York, 1990, pages 494–496; Gray, "Solid Polymer Electrolytes", ibid., pages 97–98. At page 103, Gray discloses an amorphous network system based on phosphate ester crosslinks of polyethylene glycol brought about by the reaction of $POCl_3$ with poly(ethylene oxide) glycol; J. R. M. Giles et al., Polym. Commun. 27 (1987), p. 360, and Solid State Ionics 24 (1987), p. 155.

In the design of solid polymeric electrolytes both the properties of ionic conductivity and mechanical strength must be provided. It has been found advantageous to incorporate inorganic ion salt and low molecular weight organic solvents into the solid electrolytes, as well to select polymers which enhance ionic conductivity. Cross-linking of the polymers can lead to stronger solid electrolytes, i.e. resilient thin layers of electrolyte, but cross-linking must not be to the detriment of ionic conductivity. Thermal and radiation-induced cross-linking (curing) have been extensively used for this purpose. U.S. Pat. No. 4,654,279 describes a two-phase solid polymeric electrolyte consisting of an interpenetrating network of a mechanically supporting phase consisting of crosslinked polymers, and a separate ionic conducting phase consisting of a metal salt and a complexing liquid therefore which is a poly(alkylene oxide). Poly(alkylene oxide), derivatized with acryloyl and urethane groups, is a polymer precursor for radiation-cured solid polymeric electrolytes. However, radiation-cured solid polymeric electrolytes may lack sufficient mechanical strength and toughness.

It would be advantageous if a solid polymeric matrix had the above-identified properties without the necessity of a separate curing step.

It would be advantageous if the solid polymeric matrix was a flame-retardant material. By placing a flame-retardant electrolyte in direct contact with the highly reactive lithium anode, an extra measure of safety is achieved.

SUMMARY OF THE INVENTION

The solid polymeric electrolyte of this invention comprises a compatible organophosphorous solid polymer matrix which imparts at least one of the foregoing advantageous properties to a solid polymeric electrolyte. The organophosphorus polymer has a number average molecular weight from about 1,000 to about 80,000, preferably from about 2,000 to about 50,000, and more preferably from about 3,000 to about 40,000. The molecular weight of the organophosphorus polymer, and the degree of crosslinking, affect the strength, flexibility and film-forming ability of the solid polymeric matrix electrolyte. It is desirable for the electrolyte to contain as much as 80 weight percent of electrolyte solvent without loss of these desirable properties. The organophosphorus polymers finding was within the scope of the present invention encompass polyphosphates, polyphosphonates, polyphosphites, polyphospho-amides, polyphosphines, and the like, other than the polyphosphazenes. The organophosphorus polymers of the present invention are compatible with their use in solid polymeric electrolytes comprising an inorganic ion salt and an electrolyte solvent. They are particularly compatible with such use in electrochemical cells comprising a lithium-containing anode. The preferred organophosphorus polymer is exemplified by one containing the 20 repeating unit of Formula I:

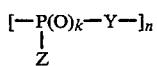
I.

In Formula I, k is O or 1; Y is selected from the group consisting of —ORO—, —SRS—, —ORS—, —N(R')RN(R')— and —N(R')R—; and Z is R' or OR'. Preferably k is 1, more preferably Y is —ORO— and k is O or 1. $R^1$ is an hydrocarbyl or oxyhydrocarbyl group, for example an alkyl, alkenyl, aryl, alkaryl, alkoxy, polyester, or poly(oxyalkylene) group of from 1 to 40 carbons atoms, preferably of from 1 to 20 carbon atoms, more preferably of from 1 to 10 carbon atoms; and R is an hydrocarbylene or oxyhydrocarbylene group, more specifically an alkylene, arylene, alkarylene, polyester, oxyalkylene, oxyarylene, oxyalkarylene, poly(oxyalkylene) or poly(oxyarylene) group of from 1 to 50 carbon atoms, preferably of from 1 to 20 carbon atoms, and more preferably of from 1 to 10 carbon atoms, preferably an alkylene, oxyalkylene or poly(oxyalkylene) group of from 2 to 40 carbons atoms, more preferably of from 2 to 20 carbons atoms, and most preferably of from 2 to 10 carbon atoms. n is an integer between about 10 and about 500, preferably between about 30 and 350, more preferably between about 20 and 300, and most preferably between 10 and 100.

When Z is OR' and Y is ORO the organophosphorus polymer is termed a polyphosphate. When Z is R' the organophosphorus polymer is termed a polyphosphonate. The polyphosphates are preferred.

In one aspect of the invention the organophosphorus polymer comprises the solid matrix portion of a solid polymeric electrolyte which also comprises a solvent and an inorganic ion salt.

In another aspect of the invention, an electrochemical cell comprises:
an anode comprising a compatible anodic material;
a cathode comprising a compatible cathodic material; and interposed therebetween a solid electrolyte which comprises:
a solid organophosphorus polymeric matrix;
an inorganic ion salt; and
a solvent;
wherein said polymeric matrix contains repeating units represented by Formula I.

In yet another aspect of the invention, an electrochemical battery comprises at least two electrochemical cells as heretofore described.

Yet another aspect of the invention is a method of making a solid electrolyte which comprises the steps of forming a mixture comprising a solvent, an inorganic ion salt and an organophosphorus polymer having repeating units represented by Formula I.

The distinct advantages of this invention is to provide an electrolyte and an electrochemical cell which has the property of flame retardation.

DETAILED DESCRIPTION OF PREFERRED EMBODIMENTS

As noted above, this invention is directed to solid, single-phase, solvent-containing polymeric electrolytes, and in particular to those employing organophosphorus polymers as the solid polymeric matrix in the polymeric electrolyte. However, prior to describing this invention in further detail, the following terms will first be defined:

Definitions

As used herein the following terms have the following meanings.

The term "organophosphorus" compound refers to any compound containing carbon and phosphorous as principal components. The term "organophophorous polymer", on the other hand, refers to a polymer whose repeating backbone unit contains carbon and phosphorous as principal compounds.

The terms "hydrocarbyl" and "oxyhydrocarbyl" refer to monovalent moieties composed of hydrogen and carbon, and hydrogen, carbon and oxygen, respectively. The terms "hydrocarbylene" and "oxyhydrocarbylene" refer to the analogous divalent moieties. Such moieties are composed of carbon-hydrogen and oxygen-hydrogen linkages, carbon-carbon linkages (both saturated and unsaturated) and carbon-oxygen linkages (both saturated and unsaturated). Consequently, the terms encompass moieties derived from hydrocarbons, polyethers, polyesters, alcohols, esters, ethers, aldehydes, ketones, carboxylic acids, etc.

The terms "solid, single-phase polymeric electrolyte" and "solid polymeric electrolyte" refer to an ionically conducting polymeric solid, normally comprising an inorganic salt, a compatible electrolyte solvent, and a solid polymeric matrix.

The term "solid polymeric matrix", as used herein, refers to a polymer made by polymerizing or copolymerizing monomer(s) or prepolymer(s) or oligomer(s). Certain solid polymeric matrices are useful in the preparation of solid polymeric electrolytes, are well known in the art, and are described, for example, in U.S. Pat. Nos. 4,908,283 and 4,925,751, both of which are incorporated herein by reference in their entirety.

The term, "a solid polymeric matrix forming monomer or polymer precursor" refers to inorganic or organic materials which in monomeric, oligomeric or polymeric form can be polymerized, or further polymerized, as by cross-linking, preferably in the presence of a salt and a solvent, to form solid polymeric matrices which are suitable for use in solid polymeric electrolytes in electrochemical cells. Typically, the solid polymeric matrix forming monomer or polymer precursor has at least one heteroatom capable of forming donor-acceptor bonds with inorganic cations, e.g. alkali ions.

The term "compatible electrolyte solvent", or in the context of components of the solid electrolyte, just "solvent", is a low molecular weight organic plasticizer added to the electrolyte and/or the cathode composition, which may also serve the purpose of solubilizing the inorganic ion salt. The solvent is any compatible, relatively non-volatile, aprotic, relatively polar, solvent. Preferably, these materials have boiling points greater than about 80° C. to simplify manufacture and increase the shelf life of the electrolyte/battery. Typical examples of solvent are mixtures of such materials as propylene carbonate, ethylene carbonate, gamma-butyrolactone, tetrahydrofuran, glyme, diglyme, triglyme, tetraglyme, dimethyl-sulfoxide, dioxolane, sulfolane, and the like. A particularly preferred solvent is disclosed in U.S. Pat. No. 5,262,253, patent which is incorporated herein by reference in its entirety.

The term "salt" refers to any salt, for example, an inorganic salt, which is suitable for use in a solid electrolyte. Representative examples of suitable inorganic ion salts are alkali metal salts of less mobile anions of weak bases having a large anionic radius. Examples of such anions are $I^-$, $Br^-$, $SCN^-$, $ClO_4^-$, $BF_4^-$, $PF_6^-$, $AsF_6^-$, $CF_3COO^-$, $CF_3SO_3^-$, $B(C_6H_5)_4^-$ and the like. Specific examples of suitable inorganic ion salts include $LiClO_4$, $LiI$ $LiSCN$, $LiBF_4$, $LiAsF_6$, $LiCF_3SO_3$, $LiPF_6$, $NaI$, $NaSCN$, $KI$, and the like. The inorganic ion salt preferably contains at least one atom selected from the group consisting of Li, Na and K.

The term "electrochemical cell" refers to a composite structure containing an anode, a cathode, and an ion-conducting electrolyte interposed therebetween.

The "anode" refers to an electrode for the half-cell reaction of oxidation on discharge, which is typically comprised of a compatible anodic material, i.e. any material which functions as an anode in a solid electrochemical cell. Such compatible anodic materials are well known in the art and include, by way of example, lithium, lithium alloys, such as alloys of lithium with aluminum, mercury, iron, zinc and the like, and intercalation-based anodes such as carbon, tungstem oxide and the like.

The "cathode" refers to the counter-electrode to the anode and is typically composed of a compatible cathodic material (i.e. insertion compounds) which is any material which functions as a cathode in an electrochemical cell. Such compatible cathodic materials are well known to the art and include by way of example, manganese oxides, molybdenum oxides, vanadium oxides, such as $V_6O_{13}$, sulfides of molybdenum, titanium and niobium, lithiated cobalt oxides, lithiated magnaese oxides, lithiated nickel oxides, chromium oxides, copper oxides, and the like. The particular compatible cathodic material employed is not critical. The term "Reference 1" refers S. R. Sandler and W. Karo, "Polymer Synthesis", Vol. 1, Chap. 13, "Organophosphorus Polymers", Academic Press, New York, 1992, the disclosure of which is incorporated herein in its entirety.

The term "polyphosphates" refers to polymers having the repeating unit

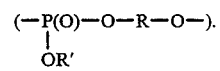

The term, "polyphosphonate" refers to polymers having the repeating unit.

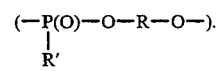

The term, "polyphosphites" refers to polymers having the repeating unit

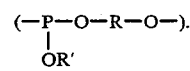

The term, "polyphospho-amides" refers to polymers having the repeating unit

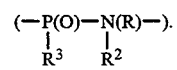

wherein R is selected from hydrogen and $C_1$–$C_7$ hydrocarbyl, oxyhydrocarbyl, hydrocarbylene and oxyhydrocarbylene and $R^2$, $R^3$ are independently selected from hydrogen and $C_1$–$C_7$ hydrocarbyl and oxyhydrocarbyl, and $R^3$ may additionally be selected from $-NR^2R^2$.

The term, "polyphosphines" or "poly(phosphine oxides)" refers to polymer having the repeating unit

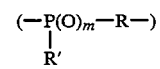

wherein m is 0 or 1, and R' is H or $C_1$–$C_7$ hydrocarbyl.

Solid Phosphate Electrolytes

One of the main reactions used to obtain polyphosphate electrolytes is that involving the reaction of alkyl dichlorophosphate with alcohols or phenols as in Reaction 1. The aromatic polyphosphates were first developed in the 950's, for example, U.S. Pat. Nos 2,616,873; 2,636,876; British Patent 644, 468, and German Patent 843,753, the disclosures of which are incorporated by reference in their entirety.

The polyphosphate esters produced by Reaction 1 can be chain-extended with typical polyester reactants, German Patent 1,117,305, the disclosure of which is incorporated by reference in its entirety. For example, bromoethyl dichlorophosphate can be condensed with 5–8 molar excess of diol to give a condensate which can be further reacted with maleic or phthalic anhydride, German Patent 1,203,464. The application of these polyphosphates as flame-retardants is disclosed in Nametz, Ind. Eng. Chem., 59, 99 (1967), the disclosure of which is incorporated by reference.

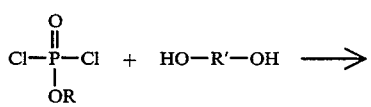

1.

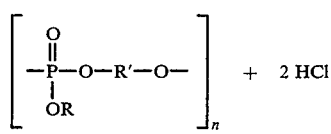

10

Another method of producing polyphosphates involves the condensation of 3-moles of a glycol with phosphorous oxychloride and subsequent reaction of the hydroxyl groups with a dicarboxylic acid as in Reactions 2 and 3 to produce a polyester polyphosphate, Reference 1, page 473.

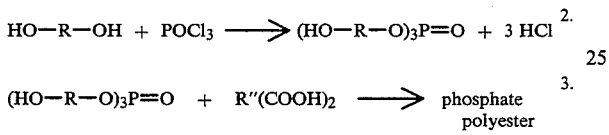

2.

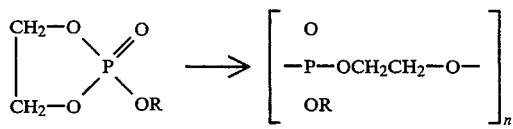

3.

The polyphosphates are also obtained by the ring-opening polymerization of cyclic phosphates as in Reaction 4, Petrov et al., Chem. Abstr., 54, 24372 (1960).

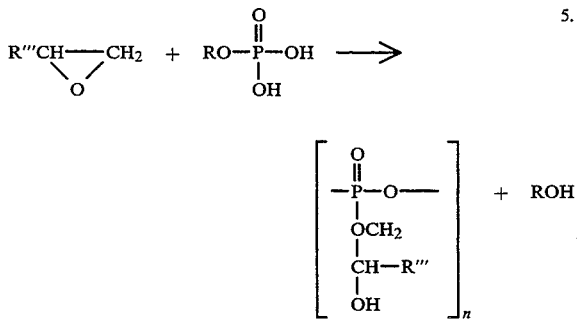

4.

Dialkylhydrogen phosphates react with epoxides to give polyphosphates as in Reaction 5, British Patent 812,390; Belgian Patent 725,477; and Japanese Patent 17,597, the disclosures of which are incorporated herein by reference.

5.

R'''CH—CH₂ + RO—P(O)(OH)—OH ⟶

[structure with —P(=O)—O—, OCH₂, CH—R''', OH]ₙ + ROH

Related polyphosphates are also produced by heating trialkyl phosphates with phosphorous pentoxide to 130° C., U.S. Pat. No. 3,378,502, the disclosure of which is incorporated by reference. The Friedel-Crafts Reaction has also been used to prepare polyphosphates by the reaction of bis-chloromethyl compounds as exemplified in Reaction 6, British Patent 524,510, the disclosure of which is incorporated by reference.

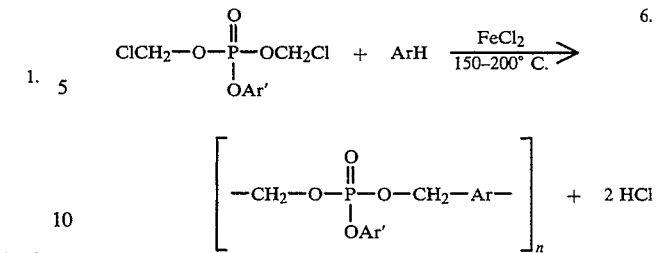

6.

Alternative methods of producing polyphosphates include those exemplified by Reactions 7 and 8, and the references following them.

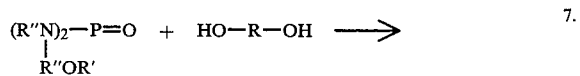

7.

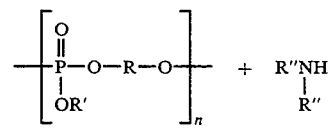

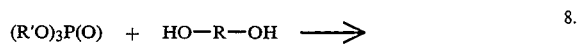

8.

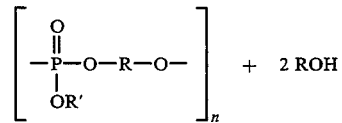

Wherein R'' is independently H or hydrocarbyl, U.S.S.R. Patent 152,572; British Patents 706,410; 679,834; 1,060,401; U.S. Pat. Nos. (2,058,394;) 2,636,876; 2,616,873;; (2,616,567; 3,549,479; 3,549,480;) German Patent 905,318; and Belgian Patent 619,217, each of which is incorporated by reference herein in its entirety.

The reaction of a trihydrocarbyl phosphate with a diol also produces, according to Reaction 8, a polyphosphate; as reported in British Patent 72,486 and D. C. Ayres et al., J. Chem. Soc., London, 1109 (1957), the disclosures of which are incorporated by reference in their entirety.

Polyphosphates are produced by the Arbuzov rearrangement, Reaction 9, U.S. Pat. No. 2,893,961, the disclosure of which is incorporated herein by

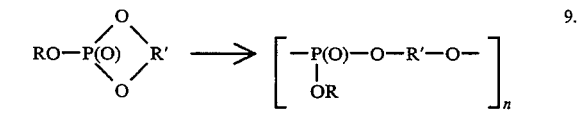

9.

reference. The anionic polymerization of cyclic esters in Reaction 9 yields polymers of high molecular weight, while cationic polymerization yields molecular weights no higher than a few thousand because of extensive chain-transfer reactions, G. Odian, "Principles of Polymerization", p. 586, Wiley, Third Edition, New York, 1991.

Copolymers of phosphates and phosphonates are prepared by heating trihaloalkyl phosphates and dialkyl phosphonates at 110°–250° C., preferably in the presence of nucleophilic catalysts such as sodium carbonate, U.S. Pat. Nos 4,297,138; 4,086,303; 4,152,371; 4,202,842; 4,335,178; and 2,372,244, the disclosures of which are incorporated by reference in their entirety. For example, the reaction of tris(β-chloroethyl) phosphate and dimethyl methylphosphonate yield the copolymer of Formula II, which leads to a cross-linked polymer on further heating.

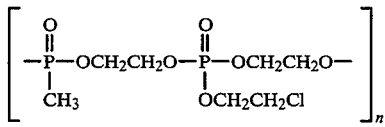
II.

The latter copolymers have been reported to be useful flame retardants for polyurethane foams and for polyesters.

The vinyl phosphates polymerize in a manner similar to that of vinyl esters and the rate of polymerization depends on the substituents present. Some typical examples of polymerization and copolymerization of vinyl phosphates are found in Reference 1, pages 481–485.

Solid Polyphosphonate Electrolytes

The reactions used to obtain polyphosphonate electrolytes are like those used to obtain polyphosphate electrolytes, i.e. the condensation polymerization of diols with di-substituted phosphonates, ring opening polymerization of epoxides or cyclic phosphonates, the Arbuzov Reaction or the free-radical polymerization of vinyl phosphonates, Reactions 10–12, see Ref. 1, pages 485–507.

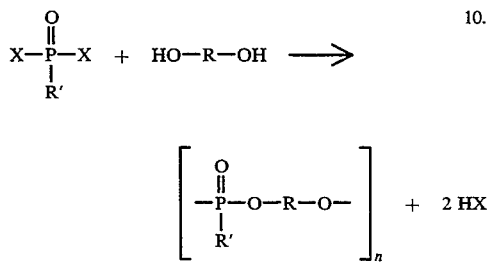
10.

Wherein X is Cl or NR$_2$''; R' and R have been previously defined, U.S. Pat Nos. 2,743,258; 2,891,915; U.S.S.R. Patent 137,673; and German Patent 1,199,500, the disclosures of which are incorporated herein by reference.

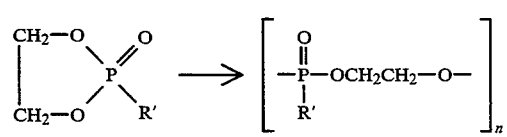
11.

Reference 1, p. 486.

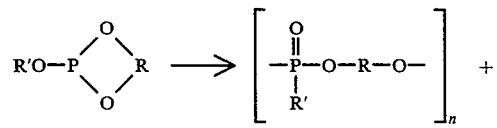
12.

-continued

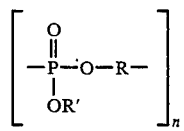

U.S. Pat. No. 2,893,961 and T. Shimidzu et at., J. Polym. Sci. Part B3, 871 (1956), the disclosures of which are incorporated herein by reference.

The self-condensation of bis(2-chloroethyl) phosphonate eliminates 1,2-dichloroethane to give a low molecular weight polyphosphonate as shown in Reaction 13 by the Arbuzov Reaction at 200°–250° C., V. V. Korshak et at., Chem Abstr. 52, 12804 (1958); Chem. Abstr., 57, 1039 (1962); and T. Shimidzu et al., J. Polym. Sci., Part B3, 871 (1956), the disclosures of which are incorporated herein by reference in their entirety.

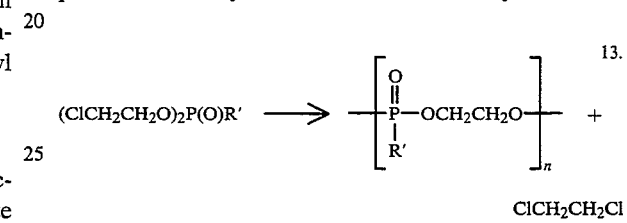
13.

The monomer in Reaction 13 is produced by the reaction of tri(chloroethyl) phosphite at 160° C., wherein R' in Reaction 13 is an alkenyl group (i.e. vinyl): followed by neutralization with NaOH at 50° C. for approximately 20 hours, U.S. Pat. No. 3,255,145 and Belgian Patent 713,066, the disclosures of which are incorporated herein by reference in their entirety.

Other Organophosphorus Polymers

Other than the polyphosphates and polyphosphonates made by various condensation reactions, the organophosphorus polymers finding use within the scope of the present invention also encompass polymers made by the free radical addition polymerization of vinyl phosphonates or phosphates and allyl phosphonates or phosphates. For example, the copolymerization diethyl vinyl phosphate with styrene, in the presence of benzoyl peroxide, yields a white solid copolymer having a softening point of 68° C. (see reference 1, page 493–507). Of particular interest are the polymerization reactions and products which form moderately hard and flexible-to-soft solids or rubber gels, some of which are listed in Reference 1, Table XIII, on page 504; A. D. F. Toy et at., J. Amer. Chem. Soc. 76,2191 (1954) the disclosure of which is incorporated herein by reference.

Polyphosphites are prepared by condensation reactions of phosphorous trichloride and its derivatives, e.g., mono-, di- and tri- alkyl or aryl phosphites, with glycols. The products can be chain extended by reaction with anhydrides and diisocyanates. Poly(hexamethylene phosphite) of molecular weight 50,000–70,000 was prepared by transisterification reaction of hexane-1,6-diol with triphenyl phosphite. Free radical addition reactions of allyl phosphites yield both glassy hard polymers and those of a rubbery, taffy-like consistency, A. D. F. Toy et al. ibid. and L. Whitehill et al., U.S. Pat. No. 2,394,829, as well as, Reference 1, pages 507–512, each of which is incorporated herein by reference.

Polyphospho-amides are prepared by reaction of phosphoric dichlorides with diamines, as well as, by the free radical polymerization of olefinic phosphorous amides, Reference 1, pages 512–519.

METHODOLOGY

Methods for preparing a solid polymeric matrix of organophosphorus polymers are well known in the art as illustrated by Reactions 1–14. The following literature examples are offered to illustrate the synthesis of organophosphorus polymers finding application in the present invention, but are not limitations to the synthetic methods which may be used.

The starting materials for the synthesis of the organophosphorus polymers of the present invention are prepared by methods well known in the art. Table I provides a tabulation of the synthetic methods used to prepare starting materials. The disclosures in the references of Table I are incorporated herein by reference in their entirety.

TABLE I

| | Ref. |
|---|---|
| $(RO)_3P + R'X \rightarrow (RO)_2P(O)R' + RX$ | a |
| $POCl_3 + R'OH \rightarrow (R'O)P(O)Cl_2 + HCl$ | b |
| $PCl_3 + 3R'OH \rightarrow (R'O)_3P$ | c |
| $POCl_3 + 3ROH + 3R'_3N \rightarrow (RO)_3 P(O) + 3R'_3NH\ Cl$ | d |
| $(R'O)\ P(O)\ Cl_2 + 2R''_2\ NH \rightarrow (R'O)\ P(O)\ (NR''_2)_2 + 2HCl$ | |

FOOTNOTES for TABLE I
a. R. T. Harvey et al., Top. Phosphorous Chem. 1, 58 (1964); U.S. Pat. No. 2,478,441.
b. G. M. Kosolapoff, "Organophosphorus Compounds", Wiley, New York, 1950.
c. U.S. Pat. No. 2,372,244.
d. C. R. Noller, "Chemistry of Organic Compounds", page 319, Third Edition, W. B. Saunders Co., Phila., 1965.

EXAMPLE I

Preparation of Poly(ethylene methylphosphonate) by the ring-opening polymerization of ethylene methylphosphite.

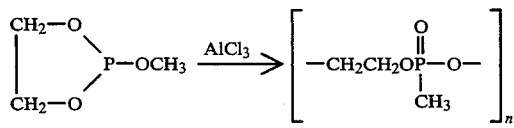

14.

To a thick-walled test tube is added 1.0 gram (0.008 mole) of dry ethylene methyl phosphite and 0.4 gram of aluminum chloride catalyst. The tube is cooled, sealed under a nitrogen stream, and placed in a 150° C. temperature bath for 8 hours to give a polymer in quantitative yield; U.S. Pat. No. 2,893,961.

EXAMPLE 2.

Polymerization of Allyl Esters of Phosphonic Acids: Diallyl Cyclohexan phosphonate To a polymer tube is added 5.0 gm of the allyl ester with 3% of benzoyl peroxide catalyst. The sample is heated for 18 hours under a nitrogen atmosphere at 87°–88° C.; J. Am Chem. Soc. 72 2275 1(1950). The reaction can be carried out in the presence of acrylolyderivatized prepolymers, or other ethyleneically unsaturated polymer precursors, i.e., monomers and oligomers, as taught in the art to achieve extensive crosslinking, higher molecular weights and greater strength in the solid polymeric matrix. Preferably, the crosslinking reactions are carried out under the influence of actinic radiation. See Reference 1, pages 494–507, for a disclosure of other phosphate and phosphonate polymers prepared from vinyl and allyl monomers. Particularly preferred are polymers which are moderately hard, flexible to soft solids, or robbery gels. (See Reference 1, pages 504–505.) The synthetic procedures of this Example are applicable to the polymerization of allyl phosphate esters as to the phosphonate esters.

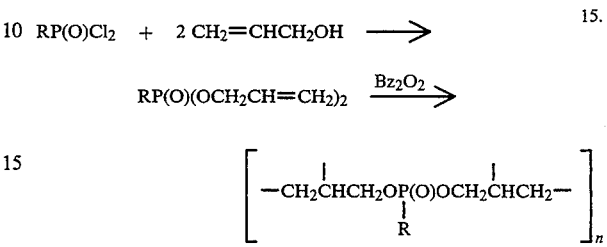

15.

EXAMPLE 3.

Preparation of a polyphosphate by the reaction of phenyl dichlorophosphate with hydroquinone.

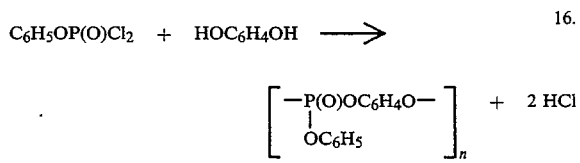

16.

To a resin kettle equipped with a mechanical stirrer, gas inlet tube, thermometer and reflux condenser with a drying tube is added 211 grams (1.0 mole) of phenyl dichlorophosphate and 115 grams (1.05 mole) of hydroquinone. While passing a slow stream of dry nitrogen over the reaction mixture, the flask is stirred vigorously for 14 hours at 168°–97° C. The hydrogen chloride gas is evolved during the reaction. After this time, the reaction mixture is heated in an oil bath at 169°–184° C. while applying vacuum of 2.5–5.0 mm Hg until bubbling practically ceases. The resulting product is a clear, light brown resin which is plastic and non-tacky at room temperature. Additional heating to 300° C. on a hot plate converts the polymer to a solid, flexible, rubbery material; U.S. Pat. No. 2,616,873.

EXAMPLE 4.

Preparation of a polyphosphite by the tranesterification reaction of hexane-1,6-diol with triphenyl phosphite.

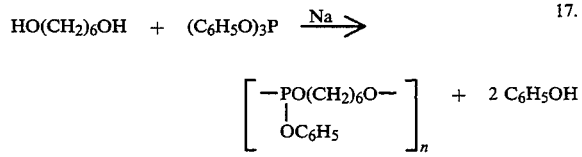

17.

To a flask equipped with a mechanical stirrer, condenser, dropping funnel, and thermometer and containing 38.8 gm (0.125 mole) of triphenyl phosphite is added dropwise over a 75 min. period at 90° C., 14.8 gm (0.125 mole) of hexane-1,6-diol containing 0.2 gm (0.01 mole) of dissolved sodium metal. During the addition a temporary clouding of the mixture clears up quickly. After standing overnight the product is a rubberlike mass, insoluble in ether and dioxane, which dissolves slowly in boiling chloroform. Concentration of the chloroform affords 12 gm (51%) phenol at a bath temperature of 130° C. (0.3 mm Hg). Raising the bath temperature to 180° C. at 0.004 mm Hg gives a little more phenol but shows no sign of boiling; D.C. Ayres et at., J. Chem. Soc., London, 1109 (1957).

Utility

The preparation of solid polymeric electrolytes from a solid polymeric matrix, and the preparation of solid electrochemical cells from a solid polymeric electrolyte, has been described in the recent patent literature, for example, by Ser. No. 08/074,107, filed Jun. 8, 1993, the disclosure of which is incorporated herein by reference in its entirety.

The organophosphorus polymer matrix of the present invention may be crosslinked with thermal or radiation treatments, or chemical groups may be appended to the organophosphorus polymer, which serve to act as sites for thermal or radiation-induced cross-linking. However, it is preferred that the organophosphorus polymers of the present invention find their principal use without the addition of separate "curing" reactions.

The following hypothetical example illustrates the construction of an electrochemical cell with an organophosphorus polymeric electrolyte.

EXAMPLE H

A solid electrochemical cell is prepared by first preparing a cathodic paste which is spread onto a current collector and is then cured, if necessary, to provide a cathode. A solid polymeric electrolyte, optionally in the form of a polymerizing solution, or in the form of a prepolymer, is then placed onto the cathode surface as a thin layer and solidified to provide the solid electrolyte composition. Then an anode is laminated onto the solid electrolyte composition to provide for a solid electrochemical cell. The specifics of this construction method are well known in the art, see for example U.S. Ser. No. 08/077,489, filed Jun. 14, 1993, the disclosure of which is incorporated herein by reference in its entirety.

The solvent-containing electrolyte is preferably prepared by combining solid polymeric matrix forming monomer(s) with an inorganic ion salt and the electrolytic solvent. The resulting composition is then uniformly coated onto a suitable substrate (e.g. an aluminum foil, a glass plate, a lithium anode, a cathode, etc.) by means of a roller, a doctor blade, a bar coder, a silk screen or spinner, to obtain a film of this composition or its solution upon the substrate. In some cases, it may be necessary to heat the composition so as to provide for a coatable material.

Preferably, the amount of material coated onto the substrate is in an amount sufficient so that the resulting solid, solvent-containing electrolyte has a thickness of no more than about 250 microns. Preferably, the solid solvent-containing electrolyte has a thickness of about 10 to about 250 microns, more preferably from about 20 to 150 microns, and even more preferably from about 50 to 90 microns.

The electrolyte composition typically comprises from about 5 to about 25 weight percent of inorganic ion salt based on the total weight of the electrolyte; preferably from about 8 to 15 wt. %.

The electrolyte composition typically comprises from about 40 to about 80 wt % solvent based on the total weight of the electrolyte; preferably from about 60 to about 80 wt %; and even more preferably about 70 wt %.

The solid electrolyte composition typically comprises from about 5 to about 30 wt % of the solid polymeric matrix based on the total weight of the electrolyte; preferably from about 12 to about 25 wt %; and even more preferably from about 17 to about 20 wt %.

In a preferred embodiment, the electrolyte composition further comprises a small amount of a film forming agent. Suitable film forming agents are well known in the art and include, by way of example, poly(ethylene oxide), poly(propylene oxide), copolymers thereof, and the like, having a number average molecular weight of at least about 100,000. Preferably, the film forming-agent is employed in an amount of from about 1 to about 10 wt %, and more preferably from about 2.5 to about 3.5 wt % based upon the total weight of the electrolyte composition. More preferably, the organophosphorus polymer has sufficient visocity and film-forming utility to eliminate the need for this ingredient.

In one embodiment the solid polymeric matrix can be dissolved into a suitable volatile solvent and the requisite amounts of the inorganic salt and the electrolyte solvent may then be added. The mixture is then applied to suitable substrate in the manner set forth above and the volatile solvents removed by conventional techniques to provide for a solid electrolyte. Suitable volatile solvents preferably have a boiling point of less than 85° C. and more preferably between about 45° and 85° C. Particularly preferred volatile solvents are aprotic solvents. Examples of suitable volatile solvents include acetonitrile, tetrahydrofuran, and the like. However, acetonitrile is not preferred if it is to directly contact the anode.

The resulting solid electrolyte is a homogeneous, single-phase material which is maintained and does not readily separate upon cooling to temperatures below room temperature.

While the invention has been described in terms of various preferred embodiments, the skilled artisan will appreciate that various modifications, substitutions, omissions and changes may be made without departing from the spirit thereof. The descriptions of subject matter in this disclosure are illustrative of the invention and are not intended to be construed as limitations upon the scope of the invention.

What is claimed is:

1. A solid polymeric electrolyte comprising a organophosphorus polymer having a molecular weight in the range of from about 1,000 to about 80,000 wherein said organophosphorus polymer is selected from the group consisting of polyphosphoro-amides and polyphosphines.

2. A solid polymeric electrolyte according to claim 1 which also comprises an inorganic ion salt and an electrolyte solvent.

3. An electrochemical cell having a solid polymeric electrolyte comprising the organophosphorus polymer of claim 1.

4. A battery comprising at least two cells according to claim 3.

5. A battery according to claim 4 wherein Y is —ORO—.

6. A battery according to claim 4 wherein k=1.

7. A battery according to claim 4 wherein R' is a poly(oxyalkylene) group.

8. A solid polymeric electrolyte comprising an organophosphorus polymer containing the repeating unit of Formula I:

$$[-P(O)_k-Y-]_n \quad \text{I.}$$
$$|$$
$$Z$$

wherein k is 0 or 1; Y is selected from the group consisting of —SRS—, —ORS—, —N(R') R N(R')—, and —N(R')R—; Z is R' or OR'; R' is a hydrocarbyl or oxyhydrocarbyl group of from 1 to 40 carbon atoms, and R is hydrocarbylene or oxyhydrocarbylene group of from 1 to 40 carbon atoms; and n is an integer having a value between about 10 and 500.

9. A solid polymeric electrolyte according to claim 8 wherein k is 1.

10. A solid polymeric electrolyte according to claim 8 wherein R' is a poly(oxyalkylene) group.

11. A solid polymeric electrolyte according to claim 8 wherein R' is a hydrocarbyl or oxyhydrocarbyl group of from 1 to 20 carbon atoms, and R is a hydrocarbylene group of from 1 to 10 carbon atoms.

12. A solid polymeric electrolyte according to claim 8 wherein n is an integer between 10 and 100.

13. A solid polymeric electrolyte according to claim 8 which also comprises an inorganic ion salt and an electrolyte solvent.

14. An electrochemical cell having a solid polymeric electrolyte comprising an organophosphorus polymer containing the repeating unit of Formula I:

$$[-P(O)_k-Y-]_n \quad \text{I.}$$
$$|$$
$$Z$$

wherein k is 0 or 1; Y is selected from the group consisting of —ORO—, —SRS—, —ORS—, —N(R') R N(R')—, and —N(R')R—; Z is R' or OR'; R' is a hydrocarbyl or oxyhydrocarbyl groups of from 1 to 40 carbon atoms, and R is hydrocarbylene or oxyhydrocarbylene group of from 1 to 40 carbon atoms; and n is an integer having a value between about 10 and 500.

15. A battery comprising at least two cells according to claim 14.

16. An electrochemical cell according to claim 14 wherein Y is —ORO—.

17. An electrochemical cell according to claim 14 wherein k is 1.

18. An electrochemical cell according to claims 14 wherein R' is a poly(oxyalkylene) group.

* * * * *